United States Patent [19]
Markowitz et al.

[11] Patent Number: 5,626,630
[45] Date of Patent: May 6, 1997

[54] MEDICAL TELEMETRY SYSTEM USING AN IMPLANTED PASSIVE TRANSPONDER

[75] Inventors: Raymond S. Markowitz, Elkins Park, Pa.; Robert E. Roy, Herndon, Va.; Xiaoguang G. Sun, King of Prussia, Pa.

[73] Assignee: AEL Industries, Inc., Lansdale, Pa.

[21] Appl. No.: 322,852

[22] Filed: Oct. 13, 1994

[51] Int. Cl.$^6$ ............................................. A61N 1/36
[52] U.S. Cl. .............................. 607/60; 607/32; 128/903
[58] Field of Search .................... 607/32, 60; 128/903

[56] References Cited

U.S. PATENT DOCUMENTS

| | | | |
|---|---|---|---|
| 3,576,554 | 4/1971 | Temps, Jr. et al. | 340/177 |
| 3,724,455 | 4/1973 | Unger | 128/903 |
| 3,798,642 | 3/1974 | Augenblick et al. | 343/7 ED |
| 3,898,984 | 8/1975 | Mandel et al. | 128/903 |
| 3,944,928 | 3/1976 | Augenblick et al. | 325/65 |
| 4,160,971 | 7/1979 | Jones et al. | 340/152 T |
| 4,281,664 | 8/1981 | Duggan | 128/696 |
| 4,361,153 | 11/1982 | Slocum et al. | 128/419 P |
| 4,494,545 | 1/1985 | Slocum et al. | 128/419 P |
| 4,531,527 | 7/1985 | Reinhold, Jr. et al. | 128/696 |
| 4,571,589 | 2/1986 | Slocum et al. | 340/870.32 |
| 4,736,207 | 4/1988 | Siikarla et al. | 343/895 |
| 4,786,907 | 11/1988 | Koelle | 342/51 |
| 4,816,839 | 3/1989 | Landt | 343/795 |
| 4,854,328 | 8/1989 | Pollack | 128/736 |
| 4,890,621 | 1/1990 | Hakky | 604/66 |
| 4,944,299 | 7/1990 | Silvian | 128/419 PG |
| 4,952,928 | 8/1990 | Carroll et al. | 340/825.54 |
| 5,099,226 | 3/1992 | Andrews | 340/572 |
| 5,113,869 | 5/1992 | Nappholz et al. | 128/903 |
| 5,153,583 | 10/1992 | Murdoch | 340/825.54 |
| 5,181,025 | 1/1993 | Ferguson et al. | 340/870.21 |
| 5,218,367 | 6/1993 | Sheffer et al. | 342/457 |
| 5,250,944 | 10/1993 | Urbas et al. | 340/870.31 |
| 5,252,962 | 10/1993 | Urbas et al. | 340/870.17 |
| 5,255,306 | 10/1993 | Melton et al. | 379/38 |
| 5,299,132 | 3/1994 | Wortham | 364/460 |
| 5,314,458 | 5/1994 | Najafi et al. | 607/60 |
| 5,319,355 | 6/1994 | Russek | 128/202.22 |
| 5,342,408 | 8/1994 | deCoriolis et al. | 607/32 |
| 5,383,915 | 1/1995 | Adams | 607/60 |
| 5,416,695 | 5/1995 | Stutman et al. | 364/413.02 |
| 5,433,736 | 7/1995 | Nilsson | 607/32 |
| 5,481,262 | 1/1996 | Urbas et al. | 128/903 |

OTHER PUBLICATIONS

Page, Raymond, "A Low Power RF ID Transponder", *RF Design*, Jul. 1993, pp. 31, 32, 34, & 36.

"A Low Power RF ID Transponder", *RF Design*, pp. 31–36 (Jul., 1993).

*Primary Examiner*—William E. Kamm
*Assistant Examiner*—Carl H. Layno

[57] ABSTRACT

A telemetry system includes a remote monitoring station, a repeater worn externally by a patient and a quasi-passive transponder attached to a device implanted in the patient. The remote monitoring station communicates to the repeater to initiate an interrogation routine between the repeater and the transponder to extract patient condition information from the implanted device. When the repeater receives the condition information, it relays it to the remote monitoring station. The transponder is specially designed to operate with an extremely low level of power, less than 1 nW/baud, and to be compatible for attachment to existing implanted devices. The transponder can operate at a very high data rate, including a rate of about 100 kbps.

39 Claims, 6 Drawing Sheets

MEDICAL TELEMETRY SYSTEM USING AN IMPLANTED PASSIVE TRANSPONDER

FIELD OF THE INVENTION

This invention relates to a telemetry system for communicating between an electronic implanted device and a remote monitoring station.

BACKGROUND OF THE INVENTION

Systems for communicating between a transponder in an electronic implanted device and a two-way telemetry device placed in close proximity to the implanted device are known in the art. For example, U.S. Pat. No. 4,361,153 discloses an external unit which transmits a carrier signal. The implanted device includes a transponder having a tuned resonant circuit for resonating at the frequency of the carrier signal so as to re-radiate a signal at the carrier frequency. The transponder also includes means for superimposing an information signal on the re-radiated signal by altering the resonance in accordance with the information signal. The re-radiated signal is received by the external device and the information signal is extracted therefrom. The resonant circuit in this patent consumes only the energy required to modulate the transponder's load impedance. Thus, the energy consumption level of this circuit is very low compared to the energy of the total signal reflected by the transponder.

Other telemetry systems for implanted devices are described in U.S. Pat. Nos. 3,576,554, 4,160,971, 4,281,664, 4,361,153, 4,494,545, 4,571,589, 4,854,328, 4,944,299, 4,952,928, 5,250,944 and 5,252,962.

Low power passive radio frequency (RF) identification transponder/reader systems are also known in the art. One system is described in Page, Raymond, "A Low Power RF ID Transponder," *RF Design*, July 1983, 31, 32, 34, 36. In this system, the reader transmits an unmodulated RF interrogation signal to a transponder attached to an object such as a rail car. The transponder receives the unmodulated RF signal, and returns a frequency doubled (i.e., second harmonic) AM modulated RF signal to a receiver placed a short distance away from the transponder. The frequency doubling and modulation are performed in the transponder by a single microwave diode. The return signal is modulated with information identifying the object. For this system to work, the reader and transponder must be in close proximity to each other.

Despite the substantial efforts in the prior art to build telemetry systems for communicating between a low-power, passive transponder implanted in an object and an interrogating device external to the object, there are still shortcomings in the existing systems. One significant shortcoming is that the interrogating device must be in close proximity to the transponder, thereby limiting the range of the telemetry system. Thus, truly "remote" monitoring of the implanted object is not possible. Another shortcoming in many prior art passive transponder systems is that the transponders rely upon the interrogating signal to gain the energy for transmission and modulation. Such systems require relatively high power interrogating signals and rectifying circuitry in the transponder. Another shortcoming in prior art telemetry systems employing passive transponders is that the antennas in the systems, and especially in the transponders, have high levels of interference and clutter, and do not function well with extremely low power signals. Yet another significant shortcoming of prior art active telemetry systems for implanted devices is that their maximum data rates (i.e., bit rates) are limited due to the use of a low carrier frequency.

These telemetry systems typically employ coil-type antennas which cannot transmit or receive high carrier frequencies. Typical data rates are about 1 to 2 kilobits per second (1 to 2 kbps), with a maximum rate of about 8 kbps.

Thus, there is still a need for a telemetry system which can interrogate an implanted object from a distant monitoring station, which employs a passive-type transponder in the implanted object, which employs an extremely low power transponder that does not require a high power interrogating signal or rectifying circuitry for operation, which employs an antenna design that performs well with extremely low power signals and which can operate at high data rates. The present invention fills that need.

SUMMARY OF THE INVENTION

The present invention provides a telemetry system for allowing an electronic device implanted in an object to communicate with a remote monitoring station. The telemetry system comprises the remote monitoring station, a passive transponder attached to the implanted device, and a two-way repeater. The electronic device has electronic condition monitoring circuitry associated therewith. The passive transponder is electrically connected to this monitoring circuitry. The transponder automatically transmits signals containing condition information when the transponder receives a proper interrogation signal from the repeater. The repeater is external to the object and in close proximity thereto. The repeater includes a first transceiver for communicating with the transponder and a second transceiver for communicating with the remote monitoring station. In this manner, the condition information received by the first transceiver is retransmitted to the remote monitoring station.

The invention also provides a method for interrogating an implanted device from a remote monitoring station by employing a repeater in proximity to the implanted device.

Unique aspects of the invention include a novel telemetry arrangement and a transponder which operates on extremely low power requirements, has a very high data rate, and employs a novel antenna design.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DESCRIPTION OF THE PREFERRED EMBODIMENT

Figure 1:
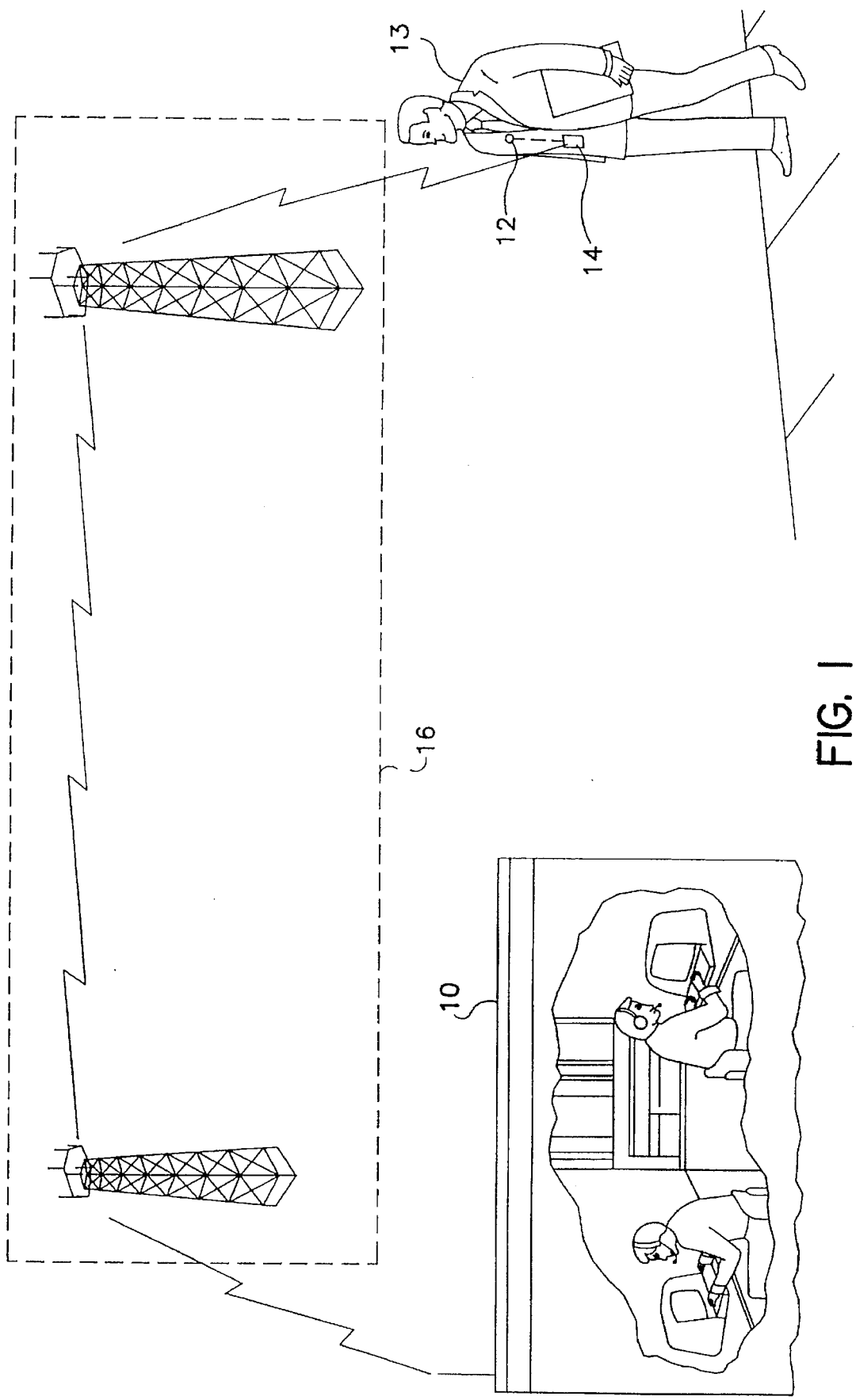
FIG. 1 is diagram of a telemetry system for an implanted device according to a preferred embodiment of the present invention.

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

Apparatus depicting the preferred embodiments of the novel telemetry system are illustrated in the drawings.

FIG. 1 shows an overview of the novel telemetry system. In the preferred embodiment of the invention, the telemetry system allows a remote monitoring station 10 to communicate with implanted device 12 through repeater 14 and cellular telephone network 16. The cellular telephone network 16, alternatively, can be a personal communications network (PCN). The device 12 is implanted in patient 13. The repeater 14 is worn externally by the patient 13 in a manner similar to a beeper or pager. Accordingly, the repeater 14 is battery powered, compact in size, and low in weight. The repeater 14 is in wireless communication with the implanted device 12. The communication path in the overall system may be one-way or two-way. In a one-way communication mode, the repeater 14 initiates an interrogation of the implanted device 12, the implanted device 12 returns an information signal to the repeater 14, and the repeater 14 relays the information to the monitoring station 10. The repeater 14 also provides a carrier signal for powering the return signal from the implanted device 12, as will be further described below. In a two-way communication mode, the monitoring station 10 initiates an information request to the repeater 14. The remaining steps are the same as in the one-way mode.

Figure 2:
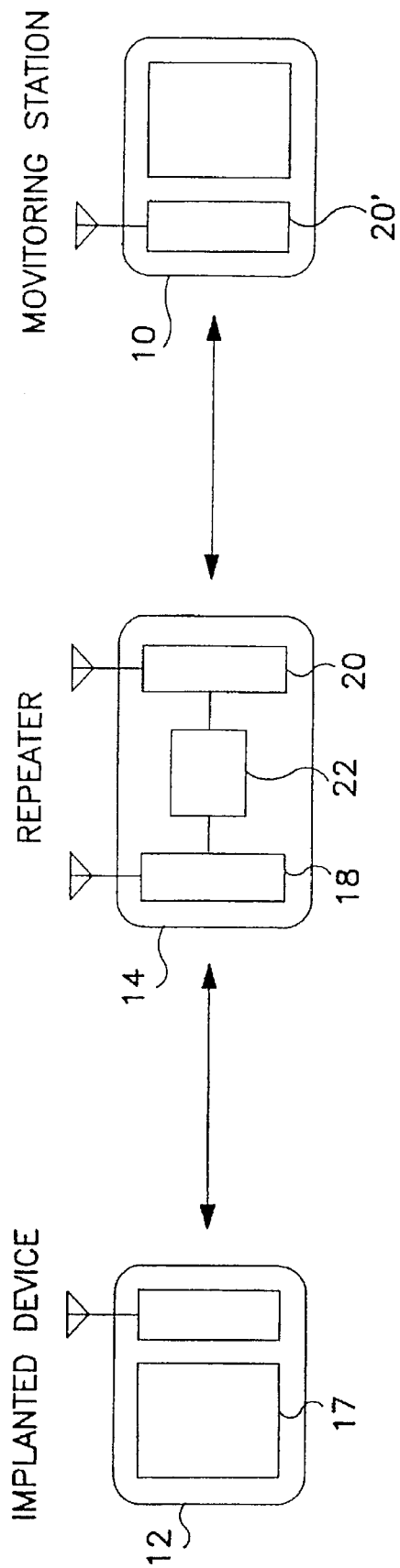
FIG. 2 is a diagram of the main components of the telemetry system in FIG. 1 and shows the communications parts of the components.

FIG. 2 shows an overview of the communications parts of the invention. An important feature of the invention is that the telemetry system employs three different types of communication devices. The first type is a transponder 17 attached to the implanted device 12. The transponder 17 is an extremely low power device (i.e., it consumes very little power, less than 1 nW/baud). It is very small in size and weight so that it can be easily incorporated onto prior art implantable devices. All parts of the transponder 17 which are external to the implantable device, and thus exposed to the patient's tissue, are bio-benign.

The second type of communication device is a transceiver 18 associated with the repeater 14. This transceiver 18 is a multi-frequency device because it transmits signals to the implanted device 12 at a first frequency and transmits signals to the monitoring station 10 at a second frequency. In an alternative embodiment of the invention, however, transceiver 18 transmits and receives at the same frequency. The transceiver 18 employs a specialized protocol, as will be described in detail below. The transceiver 18 is connected to a third type of communication device, transceiver 20, through processor/buffer 22. The transceiver 20 and the processor/buffer 22 are also associated with the repeater 14. Unlike the transceiver 18, the transceiver 20 operates on a single standard frequency for receiving and transmitting, and employs a standard protocol and baud rate. In the preferred embodiment of the invention, the transceiver 20 is a cellular communication device such as a cellular telephone which communicates with cellular networks or a PCN currently in use.

The monitoring station 10 also includes a transceiver 20' for communicating with the repeater's transceiver 20.

Figure 3:
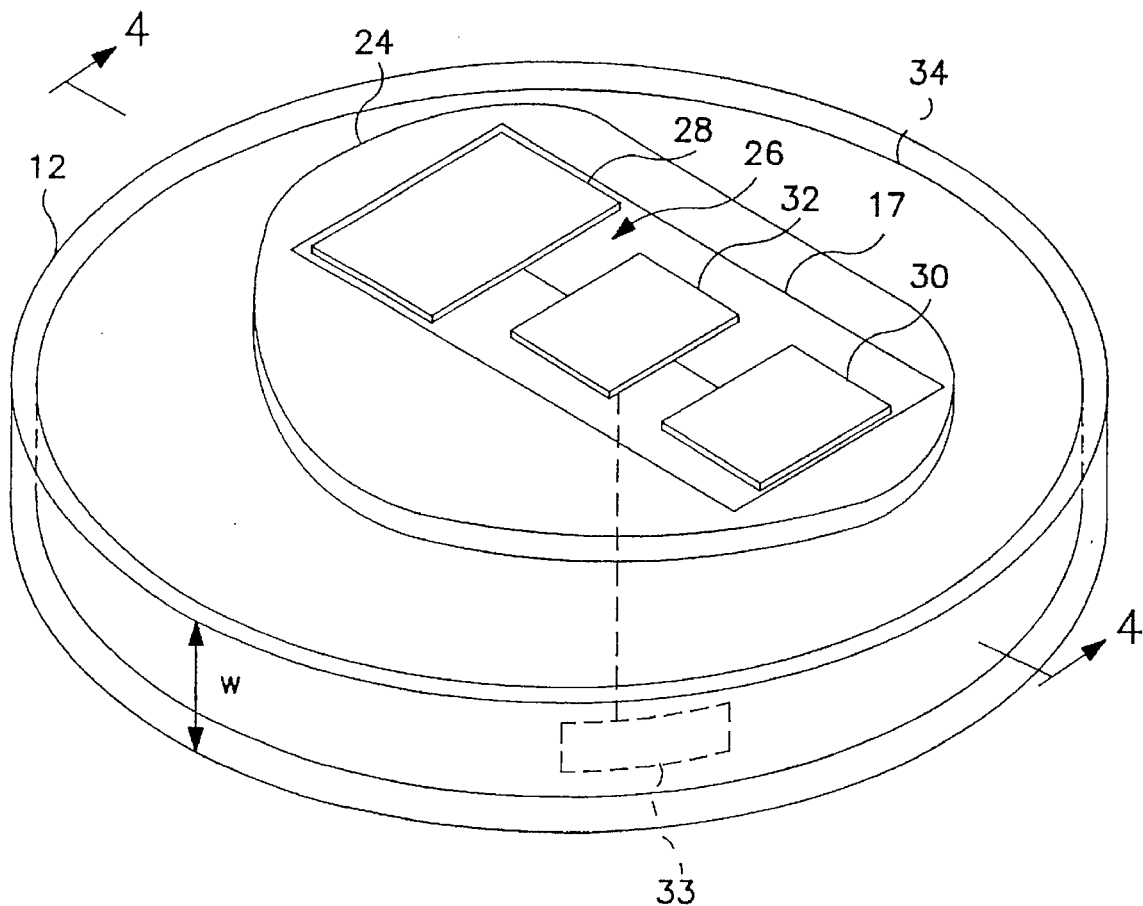
FIG. 3 is a perspective view of the implanted device showing the placement of a novel transponder thereon.

FIG. 3 shows a perspective view of the implanted device 12. The transponder 17 is disposed on a high dielectric substrate 24 attached to one or more outer surfaces of the implanted device 12. The transponder 17 includes transponder circuitry 26 having a signal receiving antenna 28 for receiving signals transmitted from the repeater 14, a signal transmitting antenna 30 for transmitting information signals back to the repeater 14 and circuitry 32 disposed therebetween. FIG. 3 also shows that the transponder circuitry 26 receives signals from one or more body condition sensor(s) /detector(s) 33 disposed inside of the implanted device 12. The sensor(s)/detector(s) 33 measure or monitor one or bodily functions. The sensor(s)/detector(s) 33 can be any prior art component sensor typically associated with an implanted device, and thus is not further described herein.

FIG. 3 depicts one embodiment of the invention wherein the implanted device 12 is a disk-shaped pacemaker. This pacemaker has a thickness w of about 7 mm. Most of the internal area of the pacemaker houses circuitry 34 for performing all of the pacemaker functions, as is well-known in the art. The sensor(s)/detector(s) 33 are included in that circuitry 34. The pacemaker electrode leads are not shown in this view.

An important feature of the invention is the arrangement of the antennas 28 and 30 with respect to the implanted device 12 and with respect to each other. Another important feature of the invention is the type of antenna employed. In the preferred embodiment, the antennas 28 and 30 are microstrip antennas. This type of antenna conforms easily to the outer surface of the implanted device 12, thereby minimizing the amount of thickness added to the implanted device 12. Also, this type of antenna can be attached to a very thin substrate on the device 12 and readily accepts an optional bio-benign protective coating.

As described more fully below, the microstrip antennas 28 and 30 may operate at different frequencies. Thus, interference and clutter are potential problems. To improve interference suppression and clutter discrimination, the antennas 28 and 30 are oriented so that their respective polarizations are orthogonal or perpendicular to each other.

Figure 4:
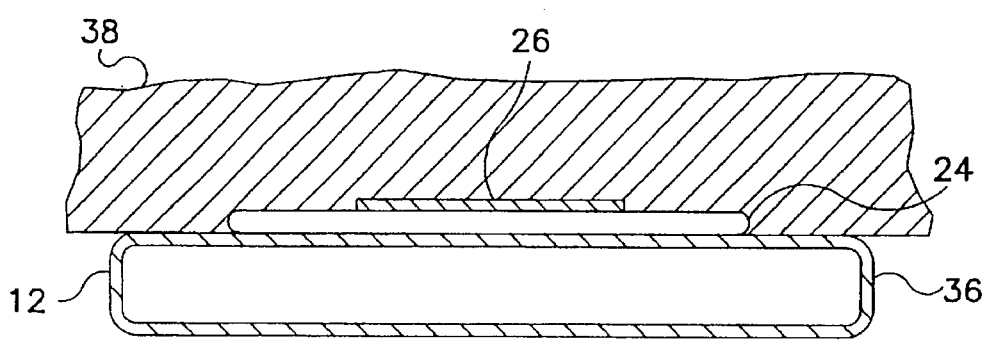
FIG. 4 is a sectional view of FIG. 3, taken along lines 4—4 in FIG. 3.

FIG. 4 is a sectional view of the implanted device 12 shown in FIG. 3, as the device 12 appears when implanted inside the patient. This view shows the device's metal case 36, dielectric substrate 24, transponder circuitry 26 disposed on the substrate 24, and the patient's bio-tissue 38. The transponder circuitry 26 may have an optional bio-benign coating thereon (not shown). The relative width of the substrate 24 with respect to the overall width of the case 36 is substantially exaggerated for illustration purposes.

Although FIG. 4 shows that the metal case 36 is hollow, in fact it is not empty. Typically, the case of a prior art implanted device 12 contains body function detection and monitoring circuitry, body function control circuitry and a battery. For example, in the case of an implanted pacemaker, the case 36 may contain a microprocessor-based heart rhythm detection and processing circuitry, heart rhythm control circuitry and an extremely long-life (e.g., 10 years) battery, labelled as pacemaker circuitry 34 in FIG. 3. FIG. 3 also illustrates one such sensor/detector circuit 33 associated with the pacemaker circuitry 34. Since the elements 33 and 34 are well known in the art, they are not described in detail herein.

Figures 5A, 5B:
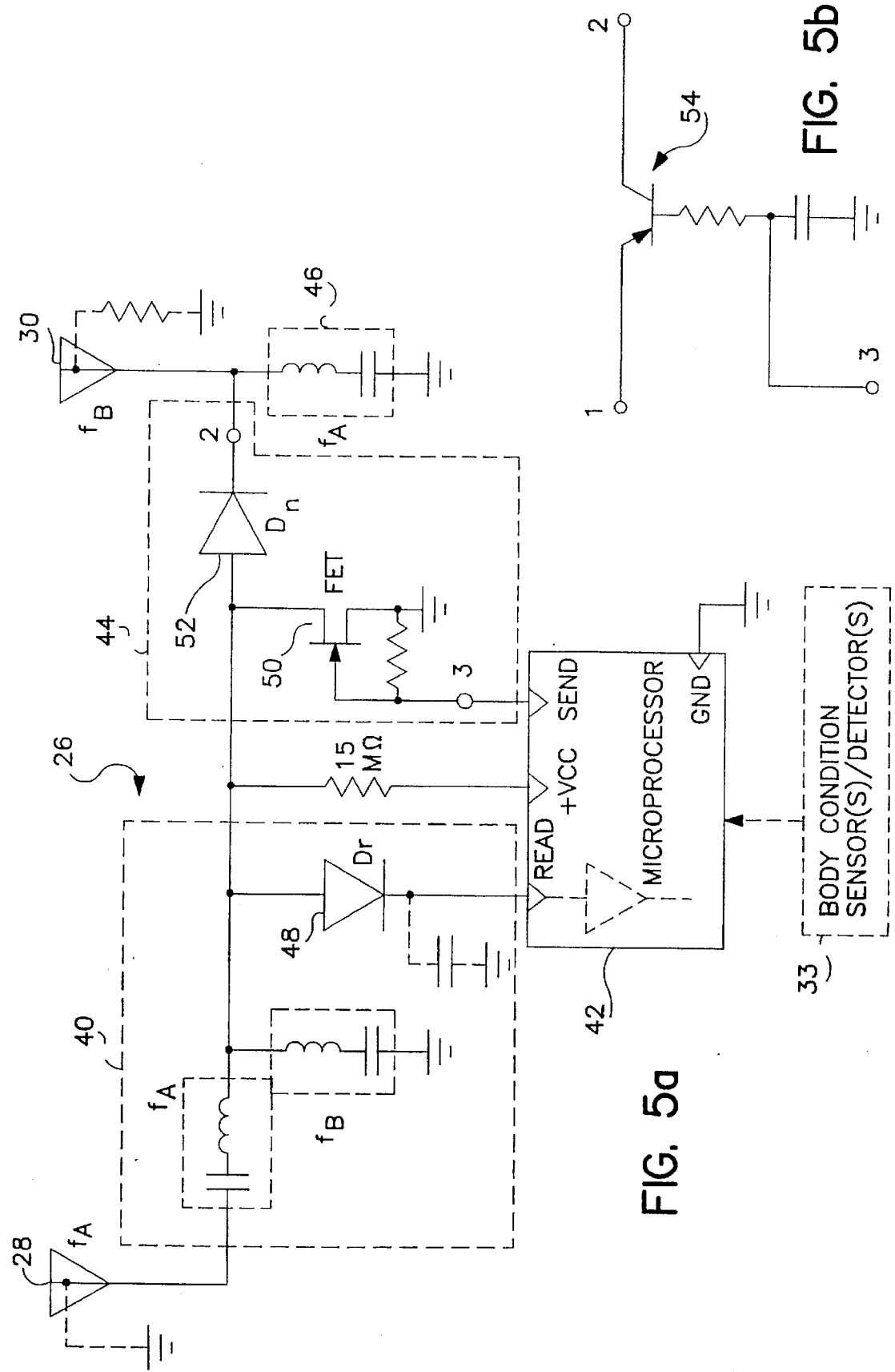
FIG. 5A is a schematic diagram of a transponder circuit associated with the implanted device according to a preferred embodiment of the present invention.
FIG. 5B is a schematic diagram of a portion of the transponder circuit for replacing a portion of the circuit shown in FIG. 5A, according to an alternative embodiment of the present invention.

FIG. 5A shows a schematic diagram of the transponder circuitry 26 of the implanted device 12. To operate as described below, the transponder circuitry 26 preferably includes at least the following six main sections:

1. signal receiving antenna 28;
2. filtering and rectifying section 40;
3. microprocessor 42;
4. a harmonic generating and modulating section 44;
5. signal transmitting filtering section 46; and
6. signal transmitting antenna 30.

The microprocessor 42 is not necessarily a physical part of the transponder circuitry 26, although it is part of the implanted device 12. For cost-effective implementation, it will be more desirable for the transponder circuitry 26 to time-share with the microprocessor associated with the prior art heart rhythm detection and processing circuitry (which is already disposed in the device's case 36). Such a microprocessor typically includes an interrogation mode which "wakes up" the circuitry. That is, when an appropriate identification signal is received by the microprocessor, it becomes fully functional and sends out information signals related to monitored body conditions (e.g., heart rhythm data, if the implanted device 12 is a pacemaker). In this embodiment, signal lines connect the microprocessor disposed in the device's case 36 to the remaining parts of the transponder circuitry 26 attached to an external surface of the case 36.

Alternatively, the microprocessor 42 is a dedicated device which is physically part of the transponder circuitry 26. In this embodiment, the microprocessor 42 is disposed on the substrate 24 with signal lines extending through the case 36 to sensor circuitry therein.

Turning to the details of the circuitry shown in FIG. 5A, the signal receiving antenna 28 is tuned to receive an RF signal at a frequency $f_A$ and pass it into the filtering and rectifying section 40. The output of the antenna 28 is connected to a bandpass filter $f_A$ and an RF trap filter $f_B$ in the section 40. The bandpass filter $f_A$ is desirable because the bandwidth of the antenna 28 will be wide due to the highly lossy tissue surrounding the implanted device 12. In the described example of the invention, frequency $f_A$ is 915 MHz and frequency $f_B$ is the second harmonic of frequency $f_A$, or 1830 MHz. In this manner, the section 40 passes the 915 MHz frequency $f_A$ signal and filters out any 1830 MHz frequency $f_B$ signals. The filtered, received signal then flows to two different paths. In the first path, the signal flows through rectifying diode 48 and into a READ terminal of the microprocessor 42. In the second path, the signal flows directly into a first input of the harmonic generating and modulating section 44.

The harmonic generating and modulating section 44 generates harmonics of the frequency of the signal output from the section 40 and modulates the harmonic signals with digital data pulses representing patient information sensed by the implanted device 12. In the disclosed embodiment, the second harmonic is employed. The harmonic generating and modulating section 44 has two inputs and one output. The first input is connected to section 40, as described above. The second input is connected to a SEND terminal of the microprocessor 42 which is a digital data output source. The output of the section 44 is connected to the signal transmitting filtering section 46 and signal transmitting antenna 30.

In one embodiment of the invention, the section 44 is a circuit comprising a high input impedance data switching transistor 50 (e.g., an N-type field effect transistor) and a harmonic generating diode 52. The positive side of the diode 52 receives the signal from the second path of the section 40 described above and also receives a signal from the drain of the switching transistor 50. As shown in FIG. 5A, the diode 52 may be optionally biased by an extremely low DC current (e.g., 0.1 μA) to increase the harmonic generation efficiency under very low RF power conditions. The negative side of the diode 52 is the output of the section 44. The source of the switching transistor 50 is connected through a resistor to the SEND terminal of the microprocessor 42 and to ground. The gate of the switching transistor 50 is connected directly to the SEND terminal.

FIG. 5B shows an alternative embodiment of the harmonic generating and modulating section 44. In this embodiment, the section 44 is a single PNP transistor 54 wherein the transistor emitter is connected to the signal from the second path of the section 40 and the collector is the output of the section 44. The base is connected through a resistor to the SEND terminal of the microprocessor 42 and through a capacitor to ground.

As noted above, the output of the harmonic generating and modulating section 44 is connected to the signal transmitting filtering section 46 and signal transmitting antenna 30. The section 46 is an RF trap filter $f_A$. The antenna 30 thus transmits a pulse code modulated signal at frequency $f_B$, which is 1830 MHz in the described example of the invention. The second harmonic was selected for the frequency $f_B$ because it allows for ultra-low power re-radiation. Of course, it should be understood that the section 44 generates other harmonics and sub-harmonics of frequency $f_A$ which are also suitable for re-radiation. Although the invention is described as employing a transmitting frequency which is a second harmonic of the receiving frequency, other harmonic frequencies are within the scope of the invention.

In the preferred embodiment of the invention, the antennas 28 and 30 are microstrip antennas. The filters $f_A$, $f_B$ and the modulation circuitry can be implemented in the microstrip transmission line on the same substrate as the antennas 28 and 30. For example, the frequency trap filters $f_A$ and $f_A$ can be implemented as microstrip stubs. A limiter can be incorporated into the microstrip transmission line associated with the antenna 28 to protect the transponder circuitry 26 against unusually high radiation levels. Either center feeds or offset feeds can be employed for the microstrip antenna design.

Figure 6A:
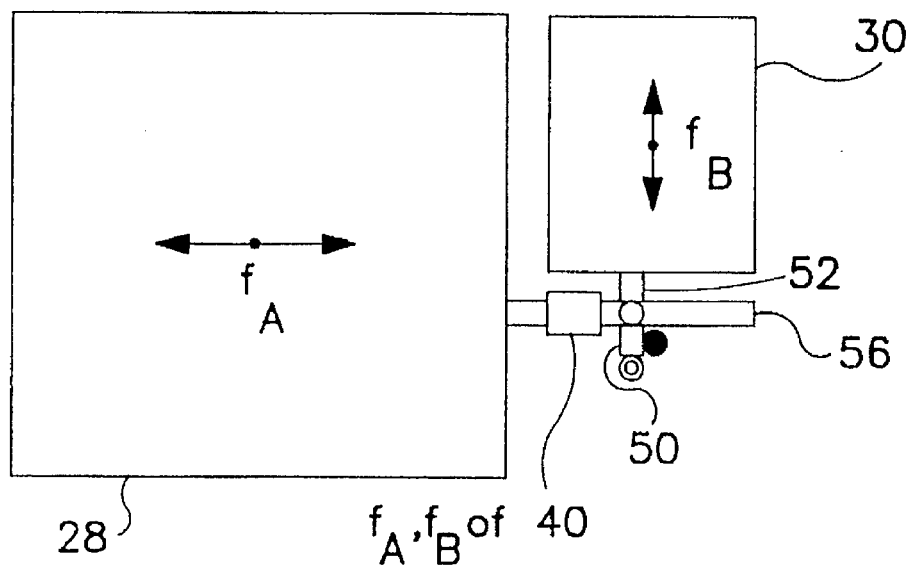
FIG. 6A is a diagrammatic representation of transponder antennas and selected transponder circuitry shown in FIG. 5A.

An important feature of the invention is the arrangement of the transponder microstrip antennas 28 and 30 with respect to each other and the manner in which they are grounded. FIG. 6A shows diagrammatically that the polarization of the antenna 28 is orthogonal to the polarization of the antenna 30. FIG. 6A also shows filters $f_A$, $f_B$ of the filtering and rectifying section 40 implemented in a microstrip transmission line 56. The antenna 30 is shown connected to the diode 52, which in turn, is connected to the switching transistor 50.

The microstrip antennas 28 or 30 also function as a DC ground by shorting the center of the antenna (either directly or through an inductive element) to a ground plate such as the implant's case. The symmetrical antenna center can be shorted because the wave impedance at this point is ideally zero. This grounding feature is desirable because many implanted devices use their cases as the DC ground for their circuit functions.

Figure 6B:
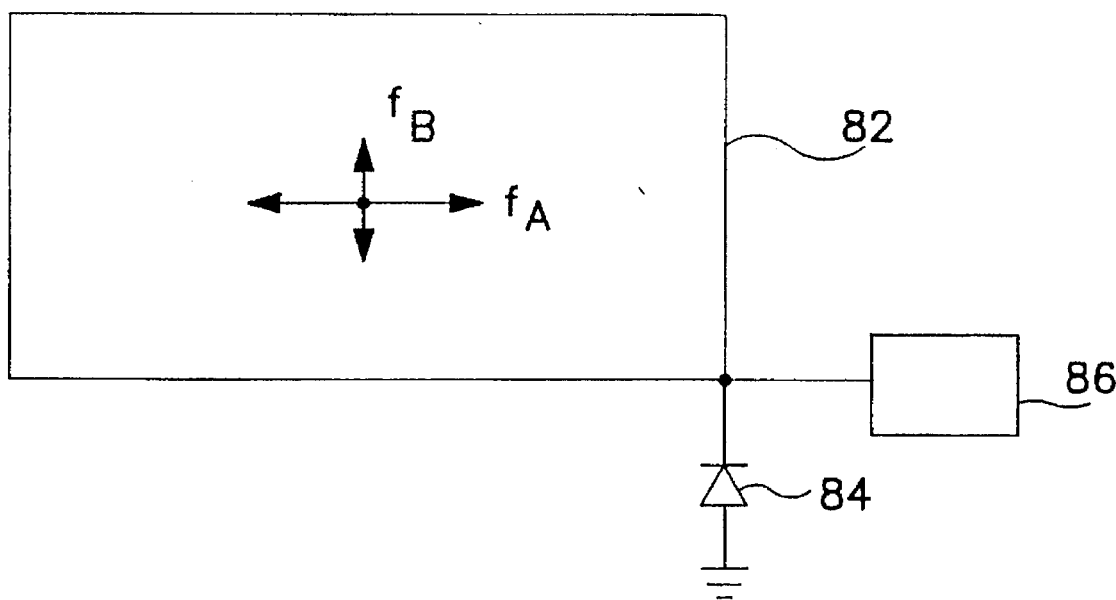
FIG. 6B is an alternative diagrammatic representation of transponder antennas and selected transponder circuitry suitable for use in FIG. 5A.

FIG. 6B shows an alternative antenna configuration which employs a single dual-frequency rectangular, corner-fed microstrip 82. This microstrip 82 resonates at frequency $f_A$ in the long direction and at frequency $f_B$ in the orthogonal direction. Again, the two polarizations are orthogonal. The center of the rectangular microstrip is also shorted. In the embodiment described herein, the rectangle has a 2:1 dimensional ratio, reflecting the ratio between the two frequencies. Shunt diode 84 connected at the corner feed performs harmonic generation and detection. This alternative configuration simplifies the circuitry necessary to perform these functions. Element 86 includes the filtering, biasing and switching circuitry.

Figure 7:
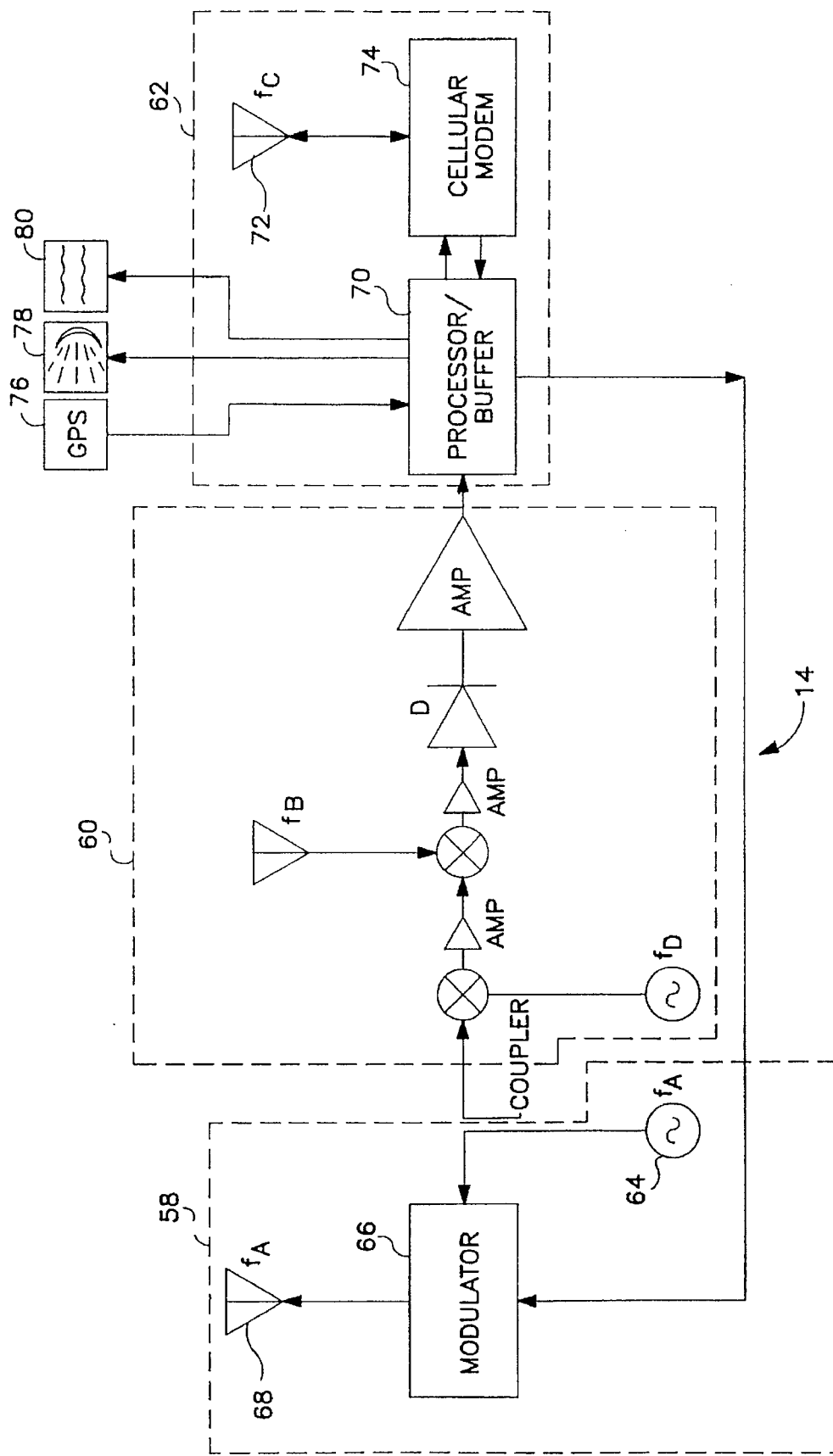
FIG. 7 is a block diagram of a repeater associated with the telemetry system.

FIG. 7 shows a block diagram of a preferred form of the repeater 14 associated with the telemetry system. The repeater 14 includes transmitting circuitry 58 for transmitting signals at a frequency $f_A$, receiving and demodulating circuitry 60 for receiving and demodulating signals received at a frequency $f_B$, and communications circuitry 62 for facilitating communication between the repeater 14 and the monitoring station 10 (not shown).

The transmitting circuitry 58 includes a carrier frequency generator 64, modulator 66 and signal transmitting antenna 68. The modulator 66 receives its modulation information from processor/buffer 70. The receiving and demodulating circuitry 60 is a high sensitivity heterodyne circuit. Together, the transmitting circuitry 58 and the receiving and demodulating circuitry 60 form a first transceiver in the repeater 14, labelled as the transceiver 18 in FIG. 2.

The communications circuitry 62 includes the processor/buffer 70, signal transmitting/receiving antenna 72 and cellular modem 74 connected therebetween. The antenna 72 transmits and receives signals at a cellular frequency $f_C$. The cellular modem 74 includes a built-in auto-dial modem for interfacing with the cellular telephone network 16 shown in FIG. 1. The communications circuitry 62 forms a second transceiver in the repeater 14, labelled as the transceiver 20 in FIG. 2.

The repeater 14 optionally includes a global positioning system (GPS) receiver 76 for allowing the repeater 14 to communicate its location to the monitoring station 10. The repeater 14 also optionally includes speaker or audio indicator 78 and/or visual indicator 80 for communicating to the patient 13 that an abnormal condition is present, or for communicating sensed condition information or status information to the patient.

To improve the reliability of the communications between the repeater 14 and the implanted device 12, the transmitting and receiving antennas in the repeater 14 are also orthogonally polarized with respect to each other in same manner as described above with respect to the transponder antennas. The signal received by the antenna in the circuitry 60 may be first downconverted to a common frequency so that a commercially available heterodyne circuit chip can be employed for the remaining parts of the circuitry.

The communications protocol of the telemetry system is an important feature of the invention and is best explained with respect to FIGS. 1, 5A, 6, and 7. This protocol allows the monitoring station 10 to interrogate the implanted device 12 at any instance in time and receive back an information signal from the device 12.

To interrogate the implanted device 12, the monitoring station 10 sends an information request signal to the repeater 14 through the cellular telephone network 16 or an equivalent PCN. The information request signal is received by the repeater's communications circuitry 62 and converted into an interrogation signal. Then, the repeater's transmitting circuitry 58 modulates the carrier frequency $f_A$ with the interrogation signal and transmits the modulated signal to the implanted device 12 at time $t_1$.

The microprocessor 42 in the transponder circuitry 26 of the implanted device 12 receives the interrogation signal at its READ terminal at time $t_2$ which will be almost instantaneously after $t_1$ when RF carrier signals are employed. In response, the microprocessor 42 sends out a digital data pulse stream (i.e., a condition information signal) at time $t_3$ which contains the requested information. Time $t_3$ is a discrete time period after $t_2$.

At about time $t_3$, the signal transmitted from the repeater's transmitting circuitry 58 is no longer modulated by the interrogation signal. That is, the interrogation signal only modulates the repeater's carrier signal for a short time interval after time $t_1$. Thus, at time $t_3$, the signal from the second output path of the transponder's filtering and rectifying path 40 which flows directly into the harmonic generating and modulating section 44 is a pure carrier signal at frequency $f_A$. This pure carrier signal is frequency doubled and modulated with the digital data pulse stream to create a modulated signal at frequency $f_B$ containing the condition information. The repeater 14 receives this signal, demodulates it and sends it to the repeater's communications circuitry 62 for subsequent communication to the monitoring station 10.

If the monitoring station 10 requests the optional GPS information and the repeater 14 includes the optional GPS receiver 76, this information is also included in the packet of data sent to the station 10. If the repeater 14 includes one or both of the optional audio or visual indicators 78 and 80, the processor/buffer 70 outputs the responses which are appropriate for the received condition information. In an alternative embodiment, the monitoring station 10 determines the responses which are appropriate for audio or visual display.

When the transponder circuitry 26 time-shares a microprocessor associated with the implanted device, the interrogation signal sent out by the repeater 14 "wakes up" the microprocessor circuitry. Thus, when an appropriate identification signal is received by the microprocessor, it becomes fully functional and ready to send out information signals related to monitored body conditions. Therefore, the modulation of the repeater's carrier frequency $f_A$ is for identification purposes only. This scheme acts as a double check so that the transponder circuitry 26 only returns a modulated information signal when the repeater 14 unequivocally desires to address the implanted device 12 associated with that particular patient. Of course, the repeater 14 will perform a first check against causing the implanted device 12 to falsely respond by checking that the information request signal received from the monitoring station 10 is directed to the associated implanted device 12. If the signal is not appropriate for the implanted device 12, the repeater 14 will not transmit any signal from the transmitting circuitry 58.

The interrogation routine described above allows the novel system described herein to be retrofitted to existing implanted devices. However, if it is desired to implement more sophisticated interrogation routines, the microprocessor circuitry of the prior art implanted devices must be modified accordingly.

Another alternative interrogation routine dispenses with the need for a modulated interrogation signal. Certain microprocessors in implanted devices will "wake up" upon receiving a pure carrier signal. If the implanted device 12 employs such a microprocessor, it is only necessary for the monitoring station 10 to send an information request signal to the repeater 14. In response to this signal, the repeater 14 sends out a pure carrier signal at frequency $f_A$. This pure carrier signal wakes up the microprocessor and the interrogation routine continues in the same manner as described above. One disadvantage of this routine is that there is no double check protection against falsely waking up the microprocessor. Thus, the monitoring station 10 could potentially receive a condition information signal from the wrong patient.

Although the novel telemetry system is described as employing a frequency $f_B$ which is the second harmonic of frequency $f_A$, wherein the frequency $f_A$ is 915 MHz, the scope of the invention includes any interrogating frequency $f_A$ and a responding frequency $f_B$ which is the same, a superharmonic or a subharmonic of the frequency $f_A$. However, the use of a high carrier frequency such as 915 MHz enables the system to achieve a high communications data rate of about 100 kbps. This rate is over ten times greater than typical prior art telemetry data rates for implanted devices.

Other types of modulation schemes are within the scope of the invention. Due to the inherent wide-band response of the harmonic generating mechanism, other waveforms such as frequency hopping or direct sequence spread spectrum can be employed instead of a pure frequency waveform to communicate the interrogation signal to the transponder circuitry 26 and to transmit the condition information signal to the repeater 14. These schemes offer added advantages such as communication security and interference immunity.

Since the transponder communicates only with a nearby repeater, and not to a larger and more distant device, the transponder in the invention operates on extremely low power. In fact, a passive miniature transponder built in the manner described above will consume less than 1 nW/baud of energy for signal modulation. Nonetheless, if it is desired to recharge the implanted device 12 to compensate for power consumed by the transponder circuitry 26, or by other parts of the implanted device 12, the transponder circuitry 26 may include an optional battery charging circuit. This circuit can recharge the device 12 with power collected by rectifying the interrogating signal. However, to extract sufficient quantities of energy from the interrogating signal, the power level output from the repeater's transmitting circuitry 58 would have to be significantly increased from the low levels needed for operating the disclosed transponder circuit.

The novel telemetry system described herein can interrogate an implanted object from virtually any part of the world without patient involvement. A patient using the novel system is thus freed from active tasks normally required to communicate interrogated information to a remote source. The transponder circuitry drastically reduces the power requirements of the implanted object transponder to less than 1 nW/baud. The transponder antenna design provides a high level of interference suppression and clutter discrimination, even when employing extremely low power signals. The telemetry system allows for very high data rates, in the range of about 100 kbps. Furthermore, the novel telemetry system can be retrofitted to prior art implanted devices for allowing truly remote interrogation of such devices.

The present invention may be embodied in other specific forms without departing from the spirit or essential attributes thereof and, accordingly, reference should be made to the appended claims, rather than to the foregoing specification, as indicating the scope of the invention.

What is claimed is:

1. A telemetry system for allowing an electronic device implanted in an object to communicate with a remote monitoring station, the telemetry system comprising
   (a) a passive transponder attached to the implanted electronic device, the implanted electronic device having condition monitoring circuitry, the transponder being electrically connected to the monitoring circuitry, the transponder automatically receiving, encoding, and reflecting an interrogation signal containing condition information when the transponder receives the interrogation signal; and
   (b) a two-way repeater external to the object and in close proximity thereto, the repeater including
      (i) a first transceiver for generating the interrogation signal and for communicating with the transponder; and
      (ii) a second transceiver for communicating with the remote monitoring station, thereby allowing the condition information received by the first transceiver to be transmitted to the remote monitoring station.

2. A telemetry system according to claim 1 wherein the two-way repeater includes means to initiate interrogation of the device's monitoring circuitry by communicating an interrogation request to the device.

3. A telemetry system according to claim 1 wherein the object is a human body.

4. A telemetry system according to claim 1 wherein the object is an implanted heart stimulator/monitor.

5. A telemetry system according to claim 1 wherein the repeater further includes a global positioning system receiver, the location of the repeater being communicated to the remote monitoring station along with the condition information.

6. A telemetry system according to claim 1 wherein the second transceiver is a cellular telephone.

7. A telemetry system according to claim 1 wherein the repeater further includes a modulator for imparting the interrogation signal which is sent to the transponder.

8. A telemetry system according to claim 1 wherein the second transceiver is a personal communications device associated with a personal communications network.

9. A telemetry system according to claim 1 wherein the object is a person and the repeater further includes a warning signal device for warning the person when the condition information is outside of selected parameters.

10. A telemetry system according to claim 9 wherein the warning signal device is a visual indicator.

11. A telemetry system according to claim 9 wherein the warning signal device is an audio indicator.

12. A telemetry system according to claim 1 wherein the transponder includes
   (i) a first antenna for receiving an unmodulated carrier signal and a carrier signal modulated by the interrogation signal, the first antenna having an input and an output, the output being connected to an input of the condition monitoring circuitry;
   (ii) a second antenna for transmitting the condition information signals, the second antenna having an input and an output; and
   (iii) a harmonic generating diode connected at one end to the output of the first antenna and at the other end to the input of the second antenna, the diode also connected at the one end to an output of the condition monitoring circuitry,
   the condition monitoring circuitry outputting the condition information when it detects the proper interrogation signal from the output of the first antenna.

13. A telemetry system according to claim 12 wherein the condition monitoring circuitry outputs the condition information in the form of digital data, the harmonic generating diode outputting a harmonic frequency of the unmodulated carrier signal modulated by the digital data.

14. A telemetry system according to claim 12 wherein the harmonic generating diode is connected to the output of the condition monitoring circuitry through a high input impedance switching transistor.

15. A telemetry system according to claim 1 wherein the remote monitoring station includes a third transceiver for allowing two-way communication with the second transceiver of the repeater.

16. A telemetry system according to claim 15 wherein the object is a living body and the repeater further includes a warning signal device activated by a control signal from the remote monitoring station for warning the person when the condition information is outside of selected parameters.

17. A telemetry system according to claim 16 wherein the warning signal device is a visual indicator.

18. A telemetry system according to claim 16 wherein the warning signal device is an audio indicator.

19. A telemetry system according to claim 15 wherein the remote monitoring station includes means to initiate interrogation of the device's monitoring circuitry by communicating an information request to the repeater.

20. A telemetry system according to claim 15 wherein the repeater further includes a global positioning system receiver activated by a control signal from the remote monitoring station, thereby allowing the location of the repeater to be communicated to the remote monitoring station by the repeater's second transceiver.

21. A telemetry system according to claim 15 wherein the repeater further includes a modulator associated with the first transceiver for imparting the interrogation signal sent to the transponder, and a processor connected to the second transceiver for receiving an information request signal from the remote monitoring station and, in turn, causing the first transceiver to transmit the interrogation signal.

22. A telemetry system according to claim 1 wherein the transponder includes (i) a first antenna for receiving the interrogation signal, and (ii) a second antenna for transmitting the condition information signals.

23. A telemetry system according to claim 22 wherein the electronic device includes an external case and the transponder's first and second antennas are disposed on outer surfaces of the case.

24. A telemetry system according to claim 23 wherein the case is metal and the antennas are disposed on a dielectric substrate sandwiched between the antennas and the case.

25. A telemetry system according to claim 22 wherein the antennas are polarized.

26. A telemetry system according to claim 25 wherein the antennas are arranged along the surface of the case so that their polarities are mutually orthogonal.

27. A telemetry system according to claim 22 wherein the first and second antennas are microstrips.

28. A telemetry system according to claim 27 wherein the first and second antennas operate at different frequencies and are incorporated into a single, dual-frequency rectangular corner-fed microstrip.

29. A telemetry system according to claim 27 wherein the polarizations of the first and second antennas are mutually orthogonal.

30. A method for communicating with an electronic device implanted in a biological object from a remote monitoring station to receive condition information associated with the object and collected by the implanted device, the method comprising the steps of (a) sending an information request signal from the remote monitoring station to a repeater, the repeater being in close proximity to the implanted device;

(b) receiving the information request signal at the repeater, the repeater transmitting a carrier frequency signal $f_A$ in response thereto;

(c) receiving the frequency signal $f_A$ at a transponder attached to the implanted device;

(d) outputting the condition information collected by the implanted device to the transponder in response to detection by the implanted device of the frequency signal $f_A$;

(e) employing the carrier frequency signal $f_A$ in the transponder to generate a transmitting frequency signal $f_B$;

(f) modulating the transmitting frequency signal $f_B$ with the condition information and transmitting the modulated frequency signal $f_B$ to the repeater;

(g) receiving the modulated frequency signal $f_B$ at the repeater, demodulating the signal and extracting the condition information therefrom; and (h) transmitting the condition information from the repeater to the remote monitoring station.

31. A method according to claim 30 wherein the frequency signal $f_B$ is a harmonic of the frequency signal $f_A$.

32. A method according to claim 30 wherein the frequency signal $f_B$ is a second harmonic of the frequency signal $f_A$.

33. A method according to claim 30 wherein steps (a) and (h) are performed through a cellular telephone network.

34. A method according to claim 30 wherein steps (a) and (h) are performed through a personal communications network.

35. A method for communicating with an electronic device implanted in a biological object from a remote monitoring station to receive condition information associated with the object and collected by the implanted device, the method comprising the steps of (a) sending an information request signal from the remote monitoring station to a repeater, the repeater being in close proximity to the implanted device;

(b) receiving the information request signal at the repeater, the repeater generating an interrogation signal therefrom;

(c) transmitting at the repeater a carrier frequency signal $f_A$, the carrier frequency signal $f_A$ being modulated by the interrogation signal for a first period of time and being unmodulated for a second period of time subsequent to the first period of time;

(d) receiving the modulated frequency signal $f_A$ at a transponder attached to the implanted device;

(e) detecting in the implanted device whether the interrogation signal matches the particular implanted device, the detection occurring during the first period of time;

(f) outputting the condition information collected by the implanted device to the transponder if the interrogation signal matches, the outputting occurring during the second period of time;

(g) employing the carrier frequency signal $f_A$ in the transponder to generate a transmitting frequency signal $f_B$;

(h) modulating the transmitting frequency signal $f_B$ with the condition information and transmitting the modulated frequency signal $f_B$ to the repeater, the modulating and transmitting occurring during the second period of time;

(i) receiving the modulated frequency signal $f_B$ at the repeater, demodulating the signal and extracting the condition information therefrom; and (j) transmitting the condition information from the repeater to the remote monitoring station.

36. A method according to claim 35 wherein the frequency signal $f_B$ is a harmonic of the frequency signal $f_A$.

37. A method according to claim 36 wherein the frequency signal $f_B$ is a second harmonic of the frequency signal $f_A$.

38. A method according to claim 35 wherein steps (a) and (j) are performed through a cellular telephone network.

39. A method according to claim 35 wherein steps (a) and (j) are performed through a personal communications network.

* * * * *